United States Patent [19]

Gasser et al.

[11] 4,374,860

[45] Feb. 22, 1983

[54] PROCESS FOR THE PRODUCTION OF A READILY WATER MISCIBLE POWDER FORM AMYLACEOUS FOOD PRODUCT

[75] Inventors: Rupert J. Gasser; Ernest Badertscher, both of Orbe, Switzerland

[73] Assignee: Societe D'Assistance Technique Pour Produits Nestle S.A., Lausanne, Switzerland

[21] Appl. No.: 212,531

[22] Filed: Dec. 3, 1980

[30] Foreign Application Priority Data

Dec. 19, 1979 [CH] Switzerland .................... 11246/79

[51] Int. Cl.³ .............................................. A23L 1/10
[52] U.S. Cl. ...................................... 426/28; 426/48; 426/52; 426/463
[58] Field of Search ................... 426/48, 18, 28, 49, 426/52, 64, 622, 661, 43, 452, 458, 463, 471

[56] References Cited

U.S. PATENT DOCUMENTS

| | | | |
|---|---|---|---|
| 1,658,027 | 2/1928 | Bosworth | 426/64 |
| 3,630,775 | 12/1971 | Winkler | 426/471 |
| 3,674,555 | 4/1972 | Meyer et al. | 426/471 |
| 3,930,027 | 12/1975 | Kelly et al. | 426/28 |
| 4,235,965 | 11/1980 | Walon | 426/48 |
| 4,254,150 | 3/1981 | Fritze et al. | 426/18 |

*Primary Examiner*—Raymond N. Jones
*Assistant Examiner*—Elizabeth J. Curtin
*Attorney, Agent, or Firm*—Vogt & O'Donnell

[57] ABSTRACT

A readily water-miscible powder-form amylaceous food product is prepared by a process in which a first mixture of amylaceous material and water is prepared, cooked and liquefied by enzymatic hydrolysis, a second mixture of amylaceous material, water and at least part of the liquefied first mixture is prepared, cooked, liquefied by enzymatic hydrolysis and at least part thereof is spray dried. The product obtained is a powder suitable for soups, acidic beverages or instant breakfasts.

14 Claims, No Drawings

PROCESS FOR THE PRODUCTION OF A READILY WATER MISCIBLE POWDER FORM AMYLACEOUS FOOD PRODUCT

This invention relates to a process for the production of a readily water-miscible powder-form amylaceous food product.

More particularly the invention relates to a process for the production of a readily water-miscible powder-form amylaceous food product in which a mixture of an amylaceous material and water is prepared, the mixture thus prepared is liquefied by enzymatic hydrolysis and then dried.

Malt-containing products obtained from starting materials, rich in starch, such as cereals or potatoes, by enzymatic liquefaction of their starch content have been available for a considerable time. One known process for producing them comprises boiling 20% by weight of barley, corn, rice, wheat or finely ground sago, tapioca or sweet potato in water, heating the resulting thick paste with steam to beyond its boiling point to gel the starch, adding malt diastase, mixing for 2 hours at 50° C., filtering, concentrating the liquor to one third of its initial volume and adding glycero-phosphates, flavouring agents and even milk solids or meat or fish extracts, it being possible for concentration to continue to dryness. This process is expensive on account of the considerable outlay required for the concentration step, in addition to which it involves a significant loss of aroma during evaporation in vacuo, in particular a loss of the taste of malt which is partially volatile.

The production of dextrins or dextrose from starting materials rich in starch, such as cereals or potatoes, has also been carried out for a considerable time. The conventional process comprises initially liquefying an aqueous suspension of the starting material or its starch component by acid hydrolysis or by enzymatic hydrolysis using an α-amylase and then saccharifying the fluid liquor by hydrolysing it with an amyloglucosidase or β-amylase. One recent process of this type comprises subjecting raw, non-gelled granular starch to hydrolysis with α-amylase and progressively adding crude granular starch to the suspension during hydrolysis whilst at the same time progressively raising the temperature. It is possible by this process to obtain very high dry matter contents without ever reaching the gelation stage, i.e. whilst at the same time maintaining a low viscosity. The crude concentrated liquefied paste may then be used as such for any of the usual applications of maltodextrins or other liquefied starches or as a starting material for a more intensive saccharification process. Although this process saves on the concentration step, it is extremely dangerous because any contaminant present in the starting material is able to develop freely, thus seriously restricting the period for which the end food products will keep. In another known process of this type, the hydrolysis step using an α-amylase is omitted and instead an amyloglucosidase is used from the outset. Although this makes the process slower in starting, the final degree of hydrolysis which it is possible to reach, expressed in dextrose or glucose equivalents (DE), is higher. In this process, a paste of corn or potato starch (dry matter content 30%) is heated with steam to 140°–150° C., subsequently cooled by expansion to 100° C. and then to 50°–60° C. in a stream of air, mixed with a recycled part of the paste liquefied further in a converter and the resulting mixture continuously introduced into this converter. The non-recycled part of the liquefied paste is introduced into batch-type converters where saccharification takes place. DE's above 99% are obtained in this way. This process is difficult to control, particularly at the cooling level, and does not lend itself to spray drying because the glucose can only be spray dried in dilute solution.

Finally, in the specific field of the present invention, instant cereal-based breakfasts especially intended for children and presented in flake form are well known. They may be produced by preparing a paste or thick suspension of finely ground rice, oats, wheat, corn, barley or a mixture thereof and drying the resulting paste or thick suspension on drums. It is known that, by selecting suitable drying conditions, it is possible to obtain both the gelation and the enzymatic hydrolysis of the starch on the drum itself, which gives a readily digestible product which is easy to reconstitute. However, this process inevitably involves caramelisation and browning (by the Maillard reaction) of the product which alters its taste and reduces its nutritional value.

An object of the present invention is to overcome the deficiencies and disadvantages of the processes mentioned above.

The present invention provides a process for the preparation of a readily water-miscible powder-form amylaceous food product, which comprises preparing a first mixture of amylaceous material and water, cooking the mixture and liquefying it by enzymatic hydrolysis, preparing a second mixture of amylaceous material, water and at least part of the first liquefied mixture, cooking the mixture, liquefying it by enzymatic hydrolysis and spray drying at least part thereof.

The process according to the invention is preferably carried out continuously, part of the liquefied mixture being recycled to the stage of mixing of amylaceous material and water.

The process according to the present invention eliminates the need to use expensive concentration installations and operations whilst, at the same time, avoiding any reaction of the Maillard or caramelisation type. It enables a powder-form product to be obtained which has extraordinary properties of miscibility, fluidity and solubility in the absence and in the presence of heat, an intact aroma of incomparable purity and a virtually complete absence of retrogradation of the starch on storage, in other words excellent keeping properties.

To carry out the process according to the invention, it is possible to use an amylaceous material, such as a coarse meal, a fine flour or even a starch of a cereal or mixture of cereals, particularly wheat, barley, oats, rye, rice and/or corn. It is preferred to use a mill product having any degree of extraction from fine wheat flour (60% of the grain) to coarse meal (95% of the grain). It is possible to obtain a product having a particularly pleasant taste by using a composition of flour or meal comprising 80% by weight of wheat, 10% of rye and 10% of oats. In addition, it is also possible to use other vegetable materials rich in starch, such as the seeds of leguminosae and certain tubers, such as potatoes, or certain roots, such as celery.

The first mixture is preferably given a dry matter content of from 25 to 35% by weight and the second mixture a dry matter content of from 35 to 45% by weight.

To cook the mixture, it may be heated by the injection of steam to a temperature of from 130° to 160° C. for example and kept at that temperature for 15 to 60s.

It is also possible to heat it to lower temperatures by adequate means and to keep it at such temperatures for a greater length of time. In view of the viscosity of the mixture sterilised and gelled by cooking, a static mixer may be installed in the line, for example just after the steam injection nozzle.

After cooking, the mixture may be directly cooled to the hydrolysis temperature by expansion or by means of a heat exchanger, depending on the circumstances. Where cooking is carried out by the injection of steam, cooling is preferably obtained by expansion in vacuo directly in a hydrolysis chamber.

Hydrolysis is preferably carried out at a temperature of from 50° to 90° C. using malt diastase. Instead of malt, it is also possible to use a combination of commercial-grade $\alpha$ and $\beta$ amylases, for example of fungal or bacterial origin. By using a combination of enzymes, such as that present in an extract of malt diastase, it is possible to vary fluidity and sweetening power within wide limits, depending on the use for which the end product is intended. If for example it is desired to obtain a thickening powder for soups, it is possible to promote the activity of the $\alpha$-amylase which randomly fragments the starch into short chains, in other words into dextrins. If, on the other hand, it is desired to obtain a powder having a high sweetening power, for example for a beverage, it is possible to promote the activity of the $\beta$-amylase which detaches molecules of maltose one after the other from one end of the starch. In the first case, hydrolysis may be carried out in a relatively short time of the order of 10 minutes at a relatively high temperature of the order of 80° C., but without exceeding 90° C. which would inactivate the enzymes. In the second case, hydrolysis may be carried out over a relatively long period of the order of 60 minutes at a relatively low temperature of the order of 60° C., but without falling below 50° C. which would excessively slow down the action of the enzymes. Where it is desired to produce a powder for an instant breakfast, it is preferred to select intermediate conditions, namely a temperature of the order of 65° to 70° C. and a hydrolysis time of from 30 to 45 minutes. The hydrolysis temperature may be controlled very precisely by cooling the cooked mixture, in other words the cooked cereal paste, by expansion in a hydrolysis chamber under a vacuum corresponding to the vapour pressure of the mixture at the temperature selected. If the hydrolysis time selected exceeds the possible residence time in this chamber, the paste undergoing hydrolysis may be transferred to one or successively to several dwell chambers at atmospheric pressure where hydrolysis may continue at the same temperature. So far as the quantity of enzymes to be used is concerned, it depends inter alia upon the activity of the enzyme, its composition and the hydrolysis conditions. A figure which may be mentioned by way of orientation is one of the order of 5% of malt diastase extract based on the weight of the meal or flour used for producing an instant breakfast.

The process may therefore be carried out continuously with recycling or in two stages on the batch principle. That part of the liquefied mixture which is not recycled in the first case or the second liquified mixture in the second case may be sterilised, for example by the injection of steam at 115°-150° C. for 5-20s, before being spray-dried. Before this liquefied mixture, which could be termed "cereal liquor", is sterilised, nutritive supplements may be added to it, particularly skimmed milk solids or whey powder or fats for example, depending on the use for which the end product is intended. It is also possible to add some of these supplements before hydrolysis and even before cooking. In cases where it is desired to produce a powder for a soup for example, it is preferred to add fat, particularly a vegetable fat, such as palm fat, coconut fat, sunflower fat, maize fat and/or soya fat, in an amount of for example from 20 to 40% by weight, based on the meal or flour used. In this case, a fat-containing powder is obtained in which the fat is so firmly bound that it does not separate and does not form any globules when the powder is dissolved in water. This also means that the aromas trapped in the fat remain there, which provides the soup with an incomparable organoleptic quality. Finally, in cases where it is desired to produce a powder for acidic beverages, nutritive supplements, particularly lactose, may be added to the liquefied mixture before it is sterilised, after which the mixture may be subjected to fermentation, particularly using lactic bacteria, after sterilisation and before spray drying.

The present invention is illustrated by the following Examples in which the percentages quoted represent percentages by weight.

EXAMPLE 1

In a continuous process, 200 kg/h of a composition (moisture content 14%) containing 80% of wheat flour, 10% of rye flour and 10% of oatmeal are mixed with 184 kg/h of drinking water at 12° C. and 426 kg/h of recycled cereal liquor having a dry matter content of 40.4%. The mixture is heated to 135° C. by the injection of steam, passed through a static mixer, transferred to a dwell pipe and, after having thus been kept at 135° C. for a total time of 30s, is cooled to 70° C. by expansion in a double-walled, mixer-equipped sealed tank where a pressure equal to the vapour pressure of the mixture at 70° C. is maintained by means of a condenser. 10 kg/h of malt diastase extract diluted in 20 kg/h of drinking water are poured into this same tank. The gently stirred mixture stays in this first tank for 15 minutes, then passes through a circuit of 3 double-walled mixer-equipped tanks where it is kept at a temperature of 70° C. at atmospheric pressure, the residence time in each tank being 10 minutes, which gives a total hydrolysis time of 45 minutes.

The flood of liquor issuing from the last tank is divided into two streams, one of 426 kg/h which is recycled and the other of 449 kg/h (dry matter content 40.4%) which is directed to the drying line. 62 kg/h of vegetable fat containing 25% of linoleic acid are thoroughly mixed with this second stream, after which the whole is sterilised by the injection of steam at 120° C. for 20s, cooled to 70° C. by expansion to atmospheric pressure and spray-dried.

A clear, free-flowing, pleasant-smelling ochre-coloured powder is obtained which dissolves very readily in both hot and cold water and does not form any globules. This powder does not show any retrogradation of the starch after storage for several months in a metal can in an inert atmosphere and at ambient temperature. It forms a high-quality base for the preparation of instant breakfast beverages. To this end, it is possible for example to mix 786 g of this base, 14 g of salt and spices and 200 g of powdered fruits, particularly pears, and to use this mixture in an amount of 35 g diluted in 125 cc of cold milk.

EXAMPLE 2

In a process similar to that described in Example 1, except that only the first tank is used and hydrolysis is carried out using either wheat or potatoes (washed, peeled and ground) or celery roots (pared and ground) or a mixture of potatoes and celery, hydrolysis is carried out for 10 minutes at 80° to 85° C., approximately 10% of fats and/or approximately 10% of skimmed milk powder is optionally added before sterilisation by the injection of steam and spray drying and an excellent base for the preparation of soups is obtained in each case. 150 to 170 g of these powders with 10 g of spices and 14 g of salt for example added will make from 1.5 to 1.7 liters of soup.

EXAMPLE 3

In a process similar to that described in Example 1, hydrolysis is carried out at 64° C. using 8.15 kg/h of malt diastase extract diluted in 16.3 kg/h of water and 985 kg/h of liquor having a dry matter content of 35.4% issues from the last tank. 396 kg/h of this liquor are recycled and mixed with 163 kg/h of flour, 30 kg/h of skimmed milk powder and 258 kg/h of water at the beginning of the cycle. The remaining 499 kg/h are directed to the drying line. 25 kg/h of vegetable fat are thoroughly mixed with this liquor. The liquor is sterilised by the injection of steam at 120° C. for 5s, cooled to 70° C. by expansion to atmospheric pressure and then to 40° C. in a tubular heat exchanger and subsequently introduced into a fermentation tank where it is biologically acidified. To this end, the liquor is inoculated with 2% of a conventional yoghurt culture consisting of *Lactobacillus bulgaricus* and *Steptococcus thermophilus* and then left to ferment for 4 hours at 40° C. The fermented liquor is then spray dried.

A cream-coloured, free-flowing powder with a pleasant flavour is obtained, dissolving very readily even in cold water. It keeps well and forms a high-quality base for the preparation of nutritional beverages. To this end, it is possible to mix 70% of this acidified powder, 15% of flakes obtained by drum drying of the same non-acidified liquor and 15% of powdered fruits for example and to use this mixture in a quantity of 35 g diluted in 125 cc of cold milk. This gives a complete fruit-flavoured drink having a fairly thick consistency reminiscent of that of stirred yoghurt.

Further typical possibilities of application comprise for example diluting 60 g of acidified orange flavoured powder in 180 g of water before drying or diluting 30 g of acidified powder in 200 cc of orange juice. It should be noted that, even in this latter case, the drink obtained is perfectly stable and does not show any sign of separation or sedimentation.

EXAMPLE 4

In a process similar to that described in Example 1, hydrolysis is carried out for 45 minutes at 64° C. and the flood of liquor issuing from the last tank has a dry matter content of 41.1%. This flood is divided into two streams, one of 419 kg/h which is recycled and the other of 442 kg/h.

This second stream is introduced into a dwell tank where it is left standing for another 3 hours at 64° C., after which it is sterilised at 120° C. by the injection of steam, cooled to 70° C. by expansion and spray dried.

A powder having a high sweetening power is obtained, being particularly suitable for use in the preparation of nutritional beverages from the composition of which sucrose may be omitted.

EXAMPLE 5

In a process similar to that described in Example 1, hydrolysis is carried out for 10 minutes at 85° C. in a single tank. The flood issuing from this tank has a dry matter content of 40.6%. It is divided into two streams, one of 424 kg/h which is recycled and the other of 448 kg/h which is sterilised for 5s at 120° C., cooled to 70° C. and spray dried.

A powder having a low sweetening power and a high viscosity after reconstitution is obtaining, forming an ideal base for an instant soup.

EXAMPLE 6

In the line used for the production steps described in the preceding Examples, instant powders are similarly prepared successively from rice, whole wheat, yellow corn, white corn, rye, barley, oats and corn starch. All these trials are conclusive. The process remains the same. Only the dry matter content or the amount recycled may vary in cases where viscosity may present a problem during cooking, particularly in the case of barley.

EXAMPLE 7

In the line used for carrying out the production steps described in the preceding Examples, trials are carried out with two commercial-grade bacterial enzymes, an amylase and an α-amylase, starting with corn starch and potato flour. Powders having a completely neutral taste are obtained.

EXAMPLE 8

In a batch-type process, 100 kg of wheat flour (moisture content 14%) are mixed in a first stage with 200 kg of drinking water at 50° C.

The mixture is heated to 135° C. by the injection of steam, passed through a static mixer, transferred to a dwell pipe and, after having thus been held for a total time of 30s, the mixture is cooled to 64° C. by expansion in a double-walled, mixer-equipped sealed tank where a pressure equal to the vapour pressure of the mixture at 64° C. is maintained by means of a condenser.

5 kg of malt diastase extract diluted in 10 kg of drinking water are poured into this tank. The stirred mixture remains in this first tank for 15 minutes, after which it is held for 30 minutes in a second double-walled tank where the temperature is kept at 64° C. at atmospheric pressure.

In a second stage, 100 kg of wheat flour (moisture content 14%) are mixed with the liquor emanating from the first hydrolysis.

This second mixture, which has a dry matter content of 41.7%, is heated to 135° C. by the injection of steam in the same way as for the first heating operation.

Cooling to 64° C. is also carried out by expansion in a sealed tank into which 5 kg of malt diastase extract diluted in 10 kg of drinking water are again added.

After a residence time of 15 minutes, during which it is continuously stirred, the mixture is transferred to a double-jacketed tank in which the whole is kept at 64° C. for 30 minutes.

The liquor issuing from this second tank is sterilised by the injection of steam of 120° C. for 20s. The liquor is cooled by expansion to atmospheric pressure and has a dry matter content of 40.6%. It is then spray dried.

A powder similar to that described in Example 1 is obtained.

By increasing the hydrolysis time in the second tank, a powder similar to that mentioned in Example 4 is obtained.

The operations of the first and second stages described above are carried out either in one and the same installation or in two identical lines arranged in series.

We claim:

1. A process for the production of a readily water-miscible powder-form amylaceous food product which comprises preparing a first mixture of amylaceous material and water, cooking the mixture to cause gelatinization of the amylaceous material and liquefying it by enzymatic hydrolysis, preparing a second mixture having a dry matter content of from 35% to 45% by weight of additional amylaceous material, water and at least 40% by weight of the first liquefied mixture, cooking the mixture to cause gelatinization of the additional amylaceous material, liquefying it by enzymatic hydrolysis and spray drying at least part thereof.

2. A process as claimed in claim 1, which is carried out continuously, part of the liquefied mixture being recycled to the stage of mixing of amylaceous material and water.

3. A process as claimed in claim 1, wherein the amylaceous material is a meal, a flour or a starch of a cereal or mixture of cereals.

4. A process as claimed in claim 3, wherein the cereal is wheat, barley, oats, rye, rice and/or maize.

5. A process as claimed in claim 1, wherein the amylaceous material consists of meal or flour of wheat, rye and oats in a ratio by weight of 80:10:10.

6. A process as claimed in claim 1, wherein the first mixture has a dry matter content of from 25 to 35% by weight.

7. A process as claimed in claim 1, wherein the first and/or second mixture is cooked by the injection of steam to a temperature of from 130° to 160° C. and kept at that temperature for 15 to 60 s.

8. A process as claimed in claim 1, wherein after cooking, the first and/or second mixture is cooled to the hydrolysis temperature by expansion.

9. A process as claimed in claim 1, wherein hydrolysis is carried out with malt diastase at a temperature in the range from 50° to 90° C.

10. A process as claimed in claim 1, wherein at least part of the liquefied second mixture is sterilized by the injection of steam before being spray dried.

11. A process as claimed in claim 10, wherein a fat is added to the liquefied mixture before it is sterilized.

12. A process as claimed in claim 10, wherein lactose is added to the mixture before it is sterilized and the mixture is subjected to fermentation by lactic bacteria after sterilization and before spray drying.

13. A readily water-miscible powder-form cereal food product prepared by the process of claim 1.

14. A process for the production of a readily water-miscible powder-form cereal food product which comprises preparing a first mixture of cereal flour and water, cooking the mixture to cause gelatinization of starch within the cereal flour and liquefying the mixture by enzymatic hydrolysis, preparing a second mixture having a dry matter content of from 35% to 45% by weight of additional cereal flour, water and at least 40% by weight of the first liquefied mixture, cooking the mixture to cause gelatinization of starch within the additional cereal flour, liquefying the mixture by enzymatic hydrolysis and spray drying at least part thereof.

* * * * *

UNITED STATES PATENT AND TRADEMARK OFFICE
CERTIFICATE OF CORRECTION

PATENT NO. : 4,374,860

DATED : February 22, 1983

INVENTOR(S) : Rupert J. Gasser and Ernest Badertscher

It is certified that error appears in the above—identified patent and that said Letters Patent is hereby corrected as shown below:

Column 1, line 16, "terials," should read --terials--.

Column 8, line 2 of Claim 13, "claim 1" should read --claim 14--.

Signed and Sealed this

Twenty-seventh Day of September 1983

[SEAL]

Attest:

GERALD J. MOSSINGHOFF

Attesting Officer

Commissioner of Patents and Trademarks